(12) United States Patent
Jullien et al.

(10) Patent No.: US 8,678,843 B2
(45) Date of Patent: Mar. 25, 2014

(54) CONNECTOR FOR A MEDICAL DEVICE HAVING A RIGID SLEEVE AND A FLEXIBLE SEAL WITH COMPLIMENTARY SURFACE PROFILES

(75) Inventors: Elodie Jullien, Dardilly (FR); François Lucas, Montrouge (FR)

(73) Assignee: Sorin CRM S.A.S., Clamart Cedex (FR)

( * ) Notice: Subject to any disclaimer, the term of this patent is extended or adjusted under 35 U.S.C. 154(b) by 56 days.

(21) Appl. No.: 13/543,313

(22) Filed: Jul. 6, 2012

(65) Prior Publication Data

US 2013/0012046 A1    Jan. 10, 2013

(30) Foreign Application Priority Data

Jul. 6, 2011 (FR) ..................................... 11 56099

(51) Int. Cl.
*H01R 13/52* (2006.01)
(52) U.S. Cl.
USPC ............................................................ 439/283
(58) Field of Classification Search
USPC .................... 439/283–285, 271–275, 587
See application file for complete search history.

(56) References Cited

U.S. PATENT DOCUMENTS

| | | | |
|---|---|---|---|
| 3,936,125 A * | 2/1976 | Hutter | 439/283 |
| 5,730,628 A | 3/1998 | Hawkins | |
| 7,083,474 B1 | 8/2006 | Fleck et al. | |
| 7,112,080 B2 * | 9/2006 | Nicholson | 439/283 |
| 7,175,478 B2 | 2/2007 | Ollivier | |
| 7,736,191 B1 * | 6/2010 | Sochor | 439/668 |
| 8,162,684 B1 * | 4/2012 | Sochor | 439/289 |
| 8,539,988 B2 * | 9/2013 | Guedon | 141/21 |
| 2003/0073348 A1 | 4/2003 | Ries et al. | |
| 2005/0186829 A1 | 8/2005 | Balsells | |
| 2007/0202728 A1 | 8/2007 | Olson et al. | |
| 2008/0274651 A1 | 11/2008 | Boyd et al. | |

FOREIGN PATENT DOCUMENTS

| | | |
|---|---|---|
| DE | 10339958 A1 | 4/2005 |
| EP | 1641084 A1 | 3/2006 |

OTHER PUBLICATIONS

Foreign Search Report (Annexe Au Rapport De Recherche Preliminaire Relatif A La Demande De Brevet Francais No. FR 1156099 FA 754102), Feb. 10, 2012.

* cited by examiner

*Primary Examiner* — Chandrika Prasad
(74) *Attorney, Agent, or Firm* — Foley & Lardner LLP (57) ABSTRACT

A connector for a multipolar lead having a substantially cylindrical cavity that contains a stack (200) of alternating annular electrical contact elements (210) and annular isolation elements (220). The isolation elements (220) comprise an annular rigid sleeve and an annular flexible seal disposed against an annular face in an interior region of the rigid sleeve. The flexible seal extends axially from one lateral side of the rigid sleeve to the other in the interior region of the rigid sleeve. The sleeve and the seal include are immobilized relatively to each other in the axial direction by use of mating surface profiles respectively defined on an inner annular side of the sleeve and on an outer annular side of the flexible seal. In addition, each lateral side of the flexible seal is projecting with respect to the corresponding lateral sides of the rigid sleeve.

11 Claims, 8 Drawing Sheets

CONNECTOR FOR A MEDICAL DEVICE HAVING A RIGID SLEEVE AND A FLEXIBLE SEAL WITH COMPLIMENTARY SURFACE PROFILES

RELATED APPLICATIONS

The present application claims the benefit of French Application No. 11/56099 entitled "Connector For A Multipolar Lead" and filed Jul. 6, 2011, which is hereby incorporated by reference in its entirety.

FIELD

The present invention relates to "active implantable medical devices" as defined by the Jun. 20, 1990 Directive 90/395/CEE of the European Community Council, which includes devices that continuously monitor the cardiac activity and deliver if and as necessary to the heart electrical stimulation pulses for cardiac pacing, resynchronization, cardioversion and/or defibrillation in response to a rhythm disorder detected by the device. It also includes neurological devices, cochlear implants, drug pumps, and implanted biological sensors.

BACKGROUND

Active implantable medical devices have a housing generally designated as the "generator," that is mechanically and electrically connected to one or more "leads" having electrodes that contact the patient's tissue at one or more locations where it is desirable to apply stimulation pulses and/or to collect (detect) an electrical signal: e.g., myocardium, nerve, muscle, or other organ tissue.

Standardized connection systems have been developed to ensure interchangeability of leads and generators that are produced by different manufacturers. Thus, the standard called "IS-1" and "IS-4" define a number of dimensional and electrical characteristics for the leads used for cardiac pacing (i.e., the delivery of low energy level stimulation pulses to cause a heartbeat). For defibrillation or cardioversion leads, wherein higher energy "shock" stimulation pulses pass from the generator to the lead, and the electrical stresses are more severe, the standards called "DF-1" and "DF-4" define the dimensional and electrical characteristics of the lead-generator connection system.

The complexity of these leads, which already incorporate specific constraints in terms of electrical energy associated with either use, pacing or shock, is enhanced by the development of multisite devices and intracardiac biological sensors such as peak endocardial acceleration (PEA) sensors. This results in terms of connectivity, in a proliferation of connection plugs, in addition to different standards depending on the plugs.

The benefit of a single plug, subject to a single standard, with a plurality of electrical contacts to simultaneously ensure connections to various terminals of the generator for all energy levels is understandable, whether for the collection of depolarization signals, for the application of low energy stimulation pulses for pacing, or the delivery of a high energy defibrillation shock.

In this context, a single "isodiametric" connection plug, that is to say a plug with a uniform cylindrical shape, designed to be inserted in a counterpart cavity of the generator, is disclosed.

EP 1641084 A1 and its US counterpart U.S. Pat. No. 7,175,478 (both assigned to Sorin CRM S.A.S. previously known as ELA Medical) describes such an isodiametric connection plug with the outer cylindrical surface having a stack of annular electrical contact zones, constructed with conductive cylindrical rings and insulating zones designed to electrically isolate the conductive rings.

For receiving a multipolar connection plug of this type and for connecting it to the electrical circuits of the generator, connectors comprising a cavity formed similarly to the plug itself are provided. The connector cavity thus also comprises a stack of annular electrical contacts to ensure electrical contact with the corresponding conductive rings of the connection plug. In this stack, the annular elements for electrical contact are separated by isolation annular elements.

It should be understood that, unlike the IS1/DF1 connection plug standard, wherein the isolation elements are carried by the lead, under the newer IS4/DF4 standard, the isolation elements are now arranged in the cavity, which has the advantage of providing new isolation elements each time the generator is replaced.

The term "isolation" used here applies both to the sealing of the cavity relatively to the external environment, especially with respect to body fluids, and to the electrical insulation, that is to say the low voltage and high voltage insulation of the electrical contact elements of the cavity, as well as the electrical contact elements of the cavity with the outside environment.

U.S. Pat. Publication No. 2005/0186829 A1 describes a connector comprising a series of stackable pieces that snap together with alternatively the insertion of a flexible joint or of an electrical connection element. Each flexible joint, or connection element, is thus pinched between two of these counterpart pieces. The tightness of this connector is nevertheless not satisfactorily ensured at the interface between the two snap-together pieces, which leaves a risk of infiltration from the environment inside the connector, particularly at the electrical connection members. It is therefore necessary to provide an additional sealing level, for example, by gluing the snap pieces, by force-fitting such as a "press-fit," or by other similar means.

U.S. Pat. No. 7,083,474 B1 also proposes a flexible joint overmolded onto a stiffening core carrying crossing holes. The rigid core carries an abutment during stacking of the various elements of the cavity. However, because the seal is not anchored, but simply attached to the rigid core through the crossing holes, nothing prevents it from moving during the insertion of the connector plug, which may degrade the sealing and electrical insulation.

U.S. Pat. Publication No. 2003/0073348 A1 describes yet another connector, made from a stack of support elements alternately attaching seals and electrical connection elements. But the drawbacks described above (imperfect seal and necessary use of an additional level of sealing, for example, by gluing or "press-fit") still remain.

OBJECT AND SUMMARY

It is therefore an object of the present invention to provide a connector that ensures not only a precise positioning of electrical contact and isolation elements, but also a seal and electrical insulation in all circumstances, especially when the connection plug of a lead is engaged in the cavity of the connector.

Broadly, the present invention is directed to a connector for a generator of an active implantable medical device which comprises a substantially cylindrical cavity for reception of a multipolar lead, including, for example, a lead of the type disclosed in U.S. Pat. Publication No. 2005/0186829 A1 cited above, having a stack of annular elements for electrical contact separated by annular isolation elements.

The isolation elements preferably comprise an annular rigid sleeve and an annular flexible seal that form therebetween a joint, disposed in an internal area inside the rigid sleeve. The rigid sleeve and the flexible seal comprise respective means of axial immobilisation of the flexible seal relatively to the rigid sleeve, by means of conjugate (i.e., complementary or mating) surface profiles defined respectively on an inner annular side of the rigid sleeve and on an outer annular side of the flexible seal. In addition, each lateral side of the flexible seal is projecting with respect to the corresponding lateral side of the rigid sleeve.

As used herein, the term "soft" in connection with a material means a material having a hardness less than or equal to 80 Shore A, and the term "hard" in connection with a material means a material having a hardness greater than or equal to 70 Shore D.

Thus, the isolation elements of the connector of the present invention are presented in two parts, namely a rigid sleeve of generally annular shape and a flexible seal, also of generally annular shape, intended to come into contact with an insulating cylindrical zone of the connection plug so as to ensure the sealing of the cavity and the low voltage electrical insulation between two consecutive conductive rings of the connection plug.

In one embodiment, the flexible seal is disposed within the rigid sleeve, its outer annular face being pressed against the inner annular face of the rigid sleeve. In addition, the flexible seal is retained on the rigid sleeve in an axial position, that is to say in the direction of the axis of the cylindrical cavity, by the fastening means defined on the flexible seal and on the rigid sleeve. In this way, the flexible seal cannot move under any circumstances, and the seal is maintained, even when subjected to axial stresses during insertion of the connection plug into the cavity.

In addition, the projection of the lateral side of the flexible seal against the corresponding lateral side of the rigid sleeve creates, by axial compression of the flexible seal, sealing between the cavity and the external environment and removes the leakage currents between the flexible seal and the rigid sleeve.

According to one embodiment, the fastening means are formed by mating surface profiles respectively defined on an inner annular face of the rigid sleeve and on an outer annular face of the flexible seal. In one preferred embodiment, the mating surface profiles are defined by cooperating shoulders formed on the inner annular side of the rigid sleeve and on the outer annular side of the flexible seal. In an alternate embodiment, the mating surface profiles are defined by cooperating grooves and ridges (also called "ribs") formed on the outer annular side of the flexible seal and on the inner annular side of the rigid sleeve.

In one embodiment, the rigid sleeve can be formed as a single piece. In another embodiment, the rigid sleeve can be constructed of two half-sleeves that are provided with complementary lugs and notches that are molded or milled such that the two half-sleeves are then clipped or joined to each other.

In a preferred embodiment, at least one lateral side of the flexible seal is projecting outwardly with respect to the corresponding lateral side of the rigid sleeve. This structure creates an axial compression of the flexible seal between the cavity and the external environment and help to eliminate leakage currents in the joint between the flexible seal and the rigid sleeve.

According to another aspect of the invention, the electrical contact elements comprise a cage housing a resilient contact, the resilient contact comprising a metal part having a U-shaped section wound to form an open cylinder, for performing a function of soft contact with the counterpart conductive rings of the connection plug of the lead. The resilient contact may particularly be made from a single flat sheet of resilient metal cut out so as to form lamellae, and folded in order to obtain the U-shape and wound (folded about an axis) to obtain the open cylinder. Advantageously, the cage comprises two lateral walls forming axial stops for positioning of the adjacent annular isolation elements of the stack.

The connector consists of a stack formed by overmoulding of electrical contact elements and isolation elements. In this case, the melting zones between the Materials constituting the rigid sleeves and the connector realize the sealing between the electrical contact elements and between the cavity and the external environment.

Finally, the alignment and concentricity of the various elements of the cavity are provided by the electrical contact elements and the rigid sleeves of the isolation elements including an interlocking assembly.

According to another embodiment, the connector in accordance with the present invention is constructed by alternate insertion of the electrical contact elements and the isolation elements within the cavity. The isolation elements are then formed as a second annular flexible seal disposed on the outer annular side of the rigid sleeve to provide isolation between the electrical contact elements and between the cavity and the external environment.

DRAWINGS

Further features, characteristics and advantages of the present invention will become apparent to a person of ordinary skill in the art from the following detailed description of preferred embodiments of the present invention, made with reference to the drawings annexed, in which like reference characters refer to like elements, and in which:

FIG. 1b is a sectional view of the connector head of FIG. 1a;

FIG. 2b is an exploded view of the electrical contact element of FIG. 2a;

FIG. 3b is an exploded view of the isolation element of FIG. 3a;

FIG. 4b is a sectional view of the isolation element of FIG. 4a;

FIG. 5b is a sectional view of the isolation element of FIG. 5a;

FIG. 6b is an exploded perspective view of the stack of FIG. 6a;

FIG. 9b is a sectional view of the assembled isolation element of FIG. 9a.

DETAILED DESCRIPTION

Figure 1A:
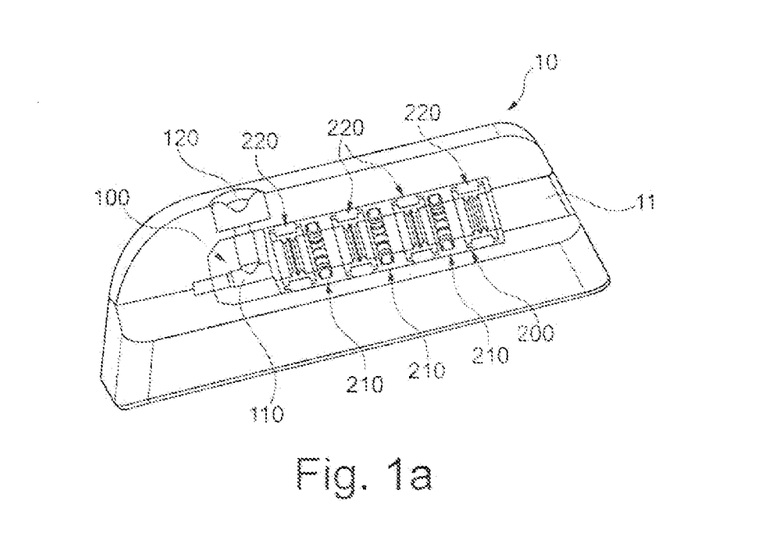
FIG. 1a is an elevated, partial cutaway perspective view of a first embodiment of a connector head according to the present invention.
Figure 1B:
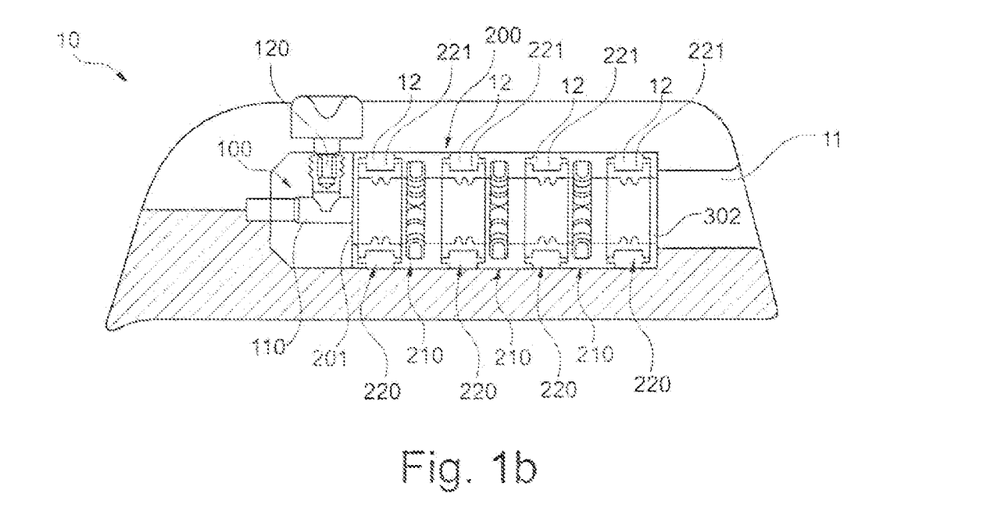

With reference to the drawings FIGS. 1-9, various examples of embodiments of the present invention will now be described. In FIGS. 1a and 1b, a connector head 10 for a generator of an active implantable medical device is shown. Connector head 10 comprises a substantially cylindrical cavity 11 for receiving, in accordance with the standard IS-4/DF-4 (ISO 27186-2010), a connection plug of a multipolar lead (not shown) so as to couple and exchange electrical signals between the generator and the heart of a patient.

EP 1641084 A1 and its counterpart U.S. Pat. No. 7,175,478 cited above describes such a four pole connection plug and is incorporated herein by reference. Specifically, this known connection plug is an isodiametric plug with on one end an axial electrical contact pin and on the body of the plug, three annular electrical contact zones made by conductive cylindrical rings. The annular electrical contact zones are separated by intercalar insulating cylindrical zones to electrically isolate the electrical contact zones from one another. Thus, the connection plug can be inserted in a single motion into the cavity 11 of the connector head 10, and simultaneously perform all the necessary electrical connections between the generator contact elements and the poles of the lead. To this end, cavity 11 must of course be equipped with contact elements corresponding to those poles present on the connection plug. These contact elements will now be described in detail in connection with the above-referenced standard.

As shown in FIGS. 1a and 1b, cavity 11 of head 10 comprises an insert 100 to allow, on the one hand, to introduce the axial pin of the connection plug into a socket 110 for the electrical connection of the axial pin with the generator, and to secure the plug in cavity 11 by means of a set screw 120.

Figure 6A:
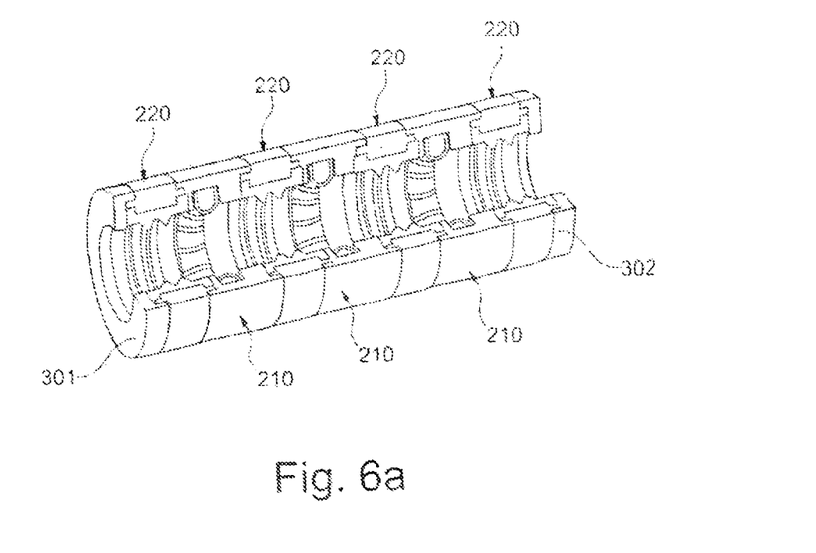
FIG. 6a is an elevated, partial cutaway perspective view of a stack of alternating electrical contact elements of FIGS. 2a and 2b and isolatation elements of FIGS. 3a and 3b.
Figure 6B:
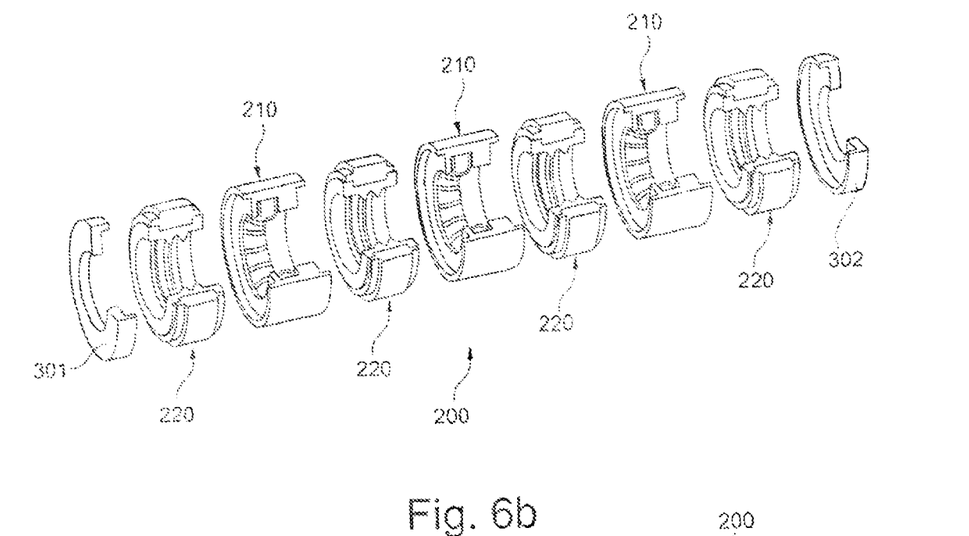

Cavity 11 further includes a stack 200 of alternating electrical contact and isolation elements that can also be seen in FIGS. 6a and 6b. More specifically, in this embodiment stack 200 includes three annular electrical contact elements 210 provided for making electrical contact with corresponding conductive rings of the connection plug in order to transmit, via the axial pin, all high and/or low voltage electrical signals from the electronics of the generator to the heart via the implanted multipolar lead and vice versa. These electrical contact elements 210 receive the connection plug of the lead and meet the insertion and extraction requirements and of electrical performance defined in the IS-4/DF-4 standard.

Figure 2A:
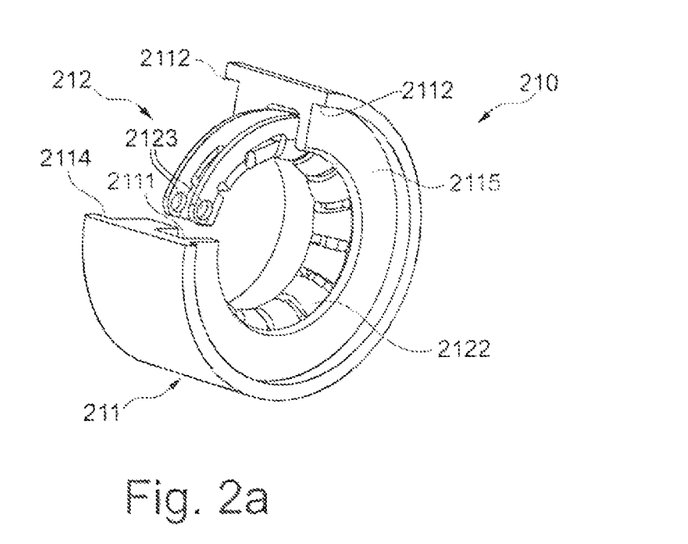
FIG. 2a is an elevated, partial cutaway perspective view of an electrical contact element of the connector head of FIGS. 1a and 1b.
Figure 2B:
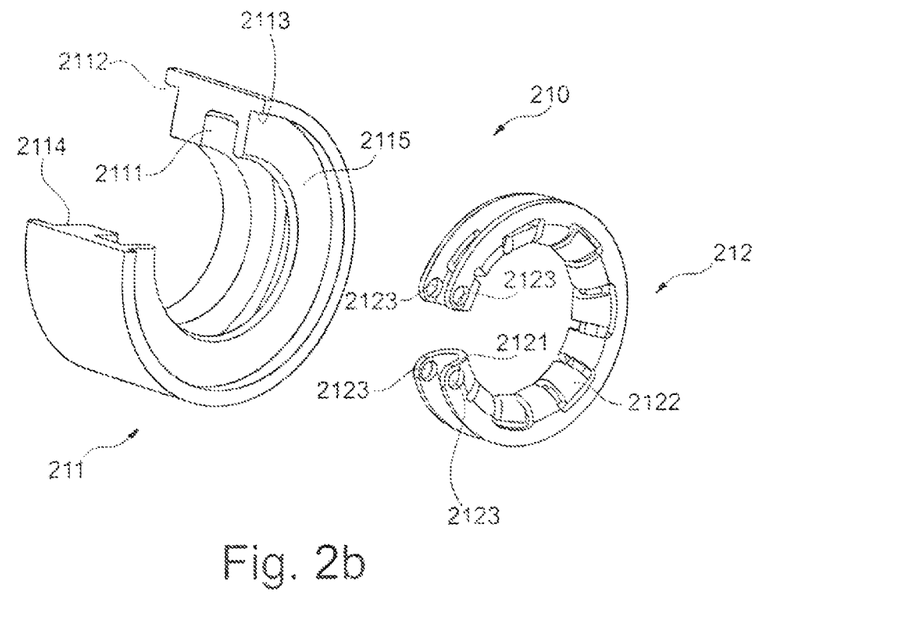

It can be can seen in more detail in FIGS. 2a and 2b that electrical contact elements 210 (or more simply "electrical contacts") are composed of two annular cylindrical sub-elements, namely a cage 211, made of a biocompatible material such as MP35N or stainless steel, and a resilient contact 212 received by cage 211 within a groove 2111 formed in its internal part, along its inner diameter. In addition, the cage 211 includes outer shoulders 2112, 2113 ensuring, as discussed below, alignment and concentricity of the various elements of the cavity.

A spring contact 212 is provided, preferably made from a single piece of implantable resilient metal having a section 2121 in a U-shape wound to form an open cylinder. Several strips or blades 2122, preferably of identical width, are distributed, preferably uniformly, around the open cylinder. Finally, four holes 2123 are drilled at the ends of the open cylinder.

Spring contact 212 performs a soft contact function with the conducting rings of the connection plug of the lead so as to obtain the best electrical contact and low contact resistance. Its U-section 2121 avoids sharp edges that can degrade components in direct contact and facilitates the shaping of the resilient contact. Holes 2123, which in the alternative may be any other equivalent structure, accept a tool for the various processes during the manufacture and installation of spring contact 212 in cage 211. The preload force exerted on holes 2123 decreases the diameter of resilient contact 212 for its introduction in the groove 2111. After removal of the preload force, resilient contact 212 expands into and is retained by groove 2111.

The two side walls 2114, 2115 of cage 211 serve as axial stops for positioning the various elements of the cavity during stacking. Its outer diameter is an electrical connection zone of the wires connecting resilient contacts 212 to the electronics of the generator, by, for example, laser or electrical welding.

Spring contact 212 is preferably made from a flat sheet of implantable resilient metal. The cutting of the shapes of blades 2122 is preferably made by flat chemical machining, water jet cutting or other industrial process. Folds are then carried out to obtain the U-shape 2121, and then to obtain the open cylinder. The cutting of blades 2122 may also be performed after the folding operation.

One can advantageously observe that the electrical contact has a small footprint that promotes the design of the rest of the cavity and of the connector plug of the lead. The U-shape 2121of spring contact 212 ensures a good electrical conductivity as the bearing surfaces between spring contact 212 and the groove 2111 guarantee a substantially uniform distribution of the support. Spring contact 212 is preferably made from a single cut and bent piece. Operations, including welding, are no longer necessary.

Of course, the number of blades 2122 and/or the thickness of the flat sheet can be increased or decreased to alter the resilience of the spring contact 212 and/or the contact resistance in order to optimize the performance of electrical contact 210.

In accordance with FIGS. 1a and 1b, electrical contacts 210 are separated along stack 200 by annular isolation elements 220 arranged opposite to the insulating zones of the connection plug so as to create electrical isolation between electrical contacts 210 and perform a sealing of the cavity 11 with respect to the external environment. Isolation elements 220 must also ensure high-voltage insulation and eliminate leak paths in their internal diameter, at the interface with the insulating zones of the connection plug, and in their outer diameter, at the interface with cavity 11.

Figure 3A:
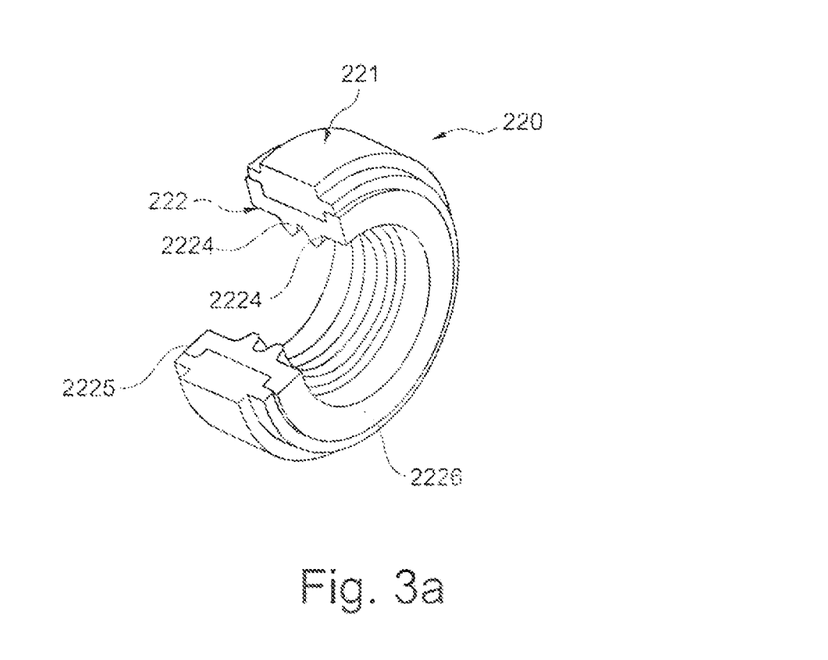
FIG. 3a is an elevated, partial cutaway perspective view of an isolation element of the connector head of FIGS. 1a and 1b.
Figure 3B:
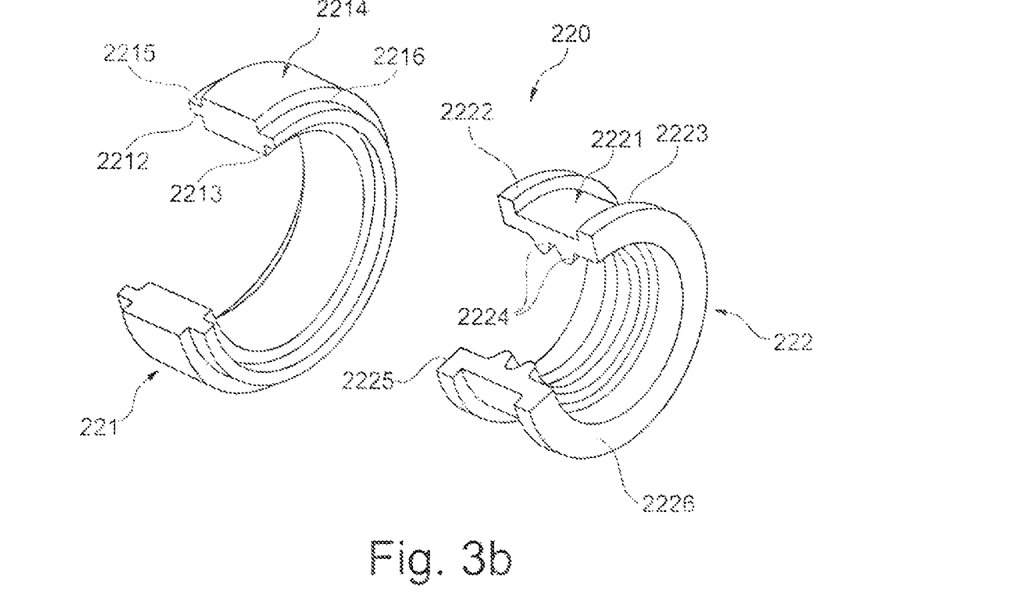

As shown in FIGS. 3a and 3b, isolation elements 220 consist of two sub-cylindrical elements, namely a rigid sleeve 221, made of a thermoplastic and more preferably a hard grade polyurethane, such as TECOTHANE (registered trademark), inside of which is disposed a flexible seal 222 made of an elastomer such as silicone or a flexible grade polyurethane. The inner annular side of flexible seal 222 is provided with sealing rings 2224 to radially compress on an insulating region of the connection plug when the latter is inserted into cavity 11, thus ensuring the insulation between two consecutive conductive rings of the connector plug and corresponding resilient electrical contacts 212.

Flexible seal 222 is placed within the rigid sleeve 221 against an inner annular side 2211 and is maintained by a blocking means which, in general, are formed by mating surface profiles respectively defined on the inner annular side 2211 of rigid sleeve 221 and the outer annular side 2221 of flexible seal 222.

In the embodiment of FIGS. 3a and 3b, the mating surface profiles are defined by inner shoulders 2212, 2213 formed on inner annular face 2211 of rigid sleeve 221 so as to cooperate with external shoulders 2222, 2223 formed on the outer annular side 2221 of flexible seal 222. This ensures that flexible seal 222 remains in position, forming a joint with rigid sleeve 221, especially when the connection plug is inserted into cavity 11.

Inner shoulders 2212, 2213 of rigid sleeve 221 create a barrier to the leakage current at the interface between rigid sleeve 221 and flexible seal 222, while outer shoulders 2215, 2216 formed on outer side 2214 of rigid sleeve 221 ensure alignment and concentricity of the various elements during their assembly by fitting with outer shoulders 2112, 2113 of cage 211, of electrical contact 210.

As can more particularly be seen in FIG. 3a, the lateral sides 2225, 2226 of flexible seal 222 are projecting relatively to the corresponding sides of rigid sleeve 221, which, for axial compression, creates a seal and remove the leakage currents between flexible seal 222 and rigid sleeve 221.

The flexible seal 222 may be molded or assembled in the inner part of rigid sleeve 221. Rigid sleeve 221 is preferably molded or machined.

The advantages of the embodiment of isolation element 220 presented in FIGS. 3a and 3b are multiple. Indeed, it combines two factors, the resiliency necessary of the shape of sealing rings 2224 and the rigidity of the outer shape of the sleeve 221. Furthermore, the association of two parts, rigid sleeve and flexible seal, ensures the axial position in order to respect the insulating zones and the radial positioning allowing the insulation at the inner diameter of flexible seal 222, as required by the DF-4 standard.

Figure 4A:
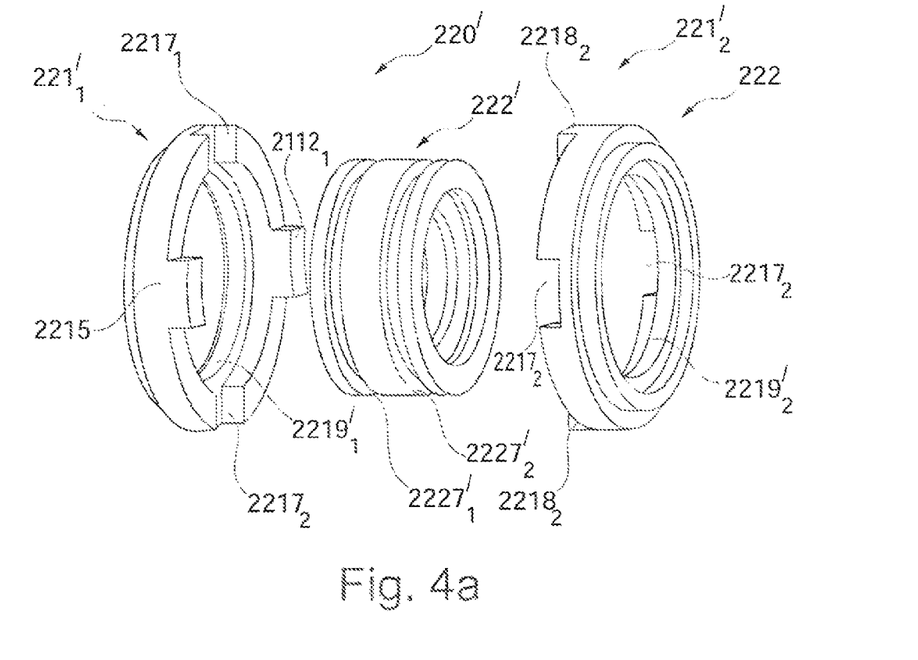
FIG. 4a is an exploded perspective view of a first embodiment of the isolation element of FIGS. 3a and 3b.
Figure 4B:
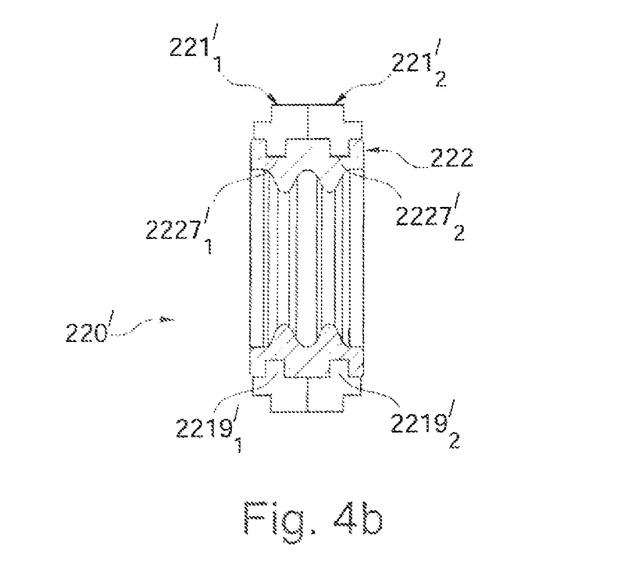
Figure 5A:
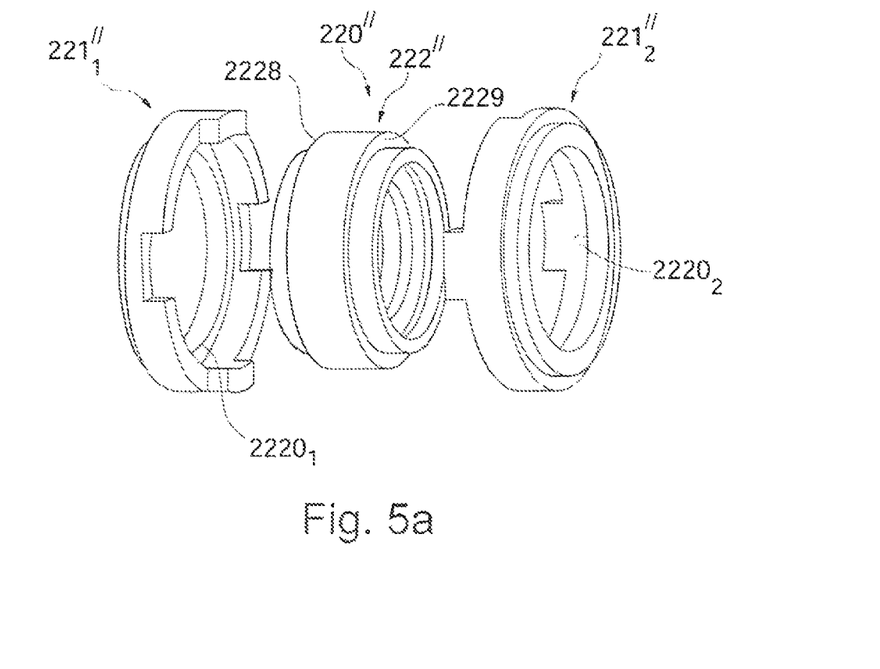
FIG. 5a is an exploded perspective view of a second embodiment of the isolation element of FIGS. 3a and 3b.
Figure 5B:
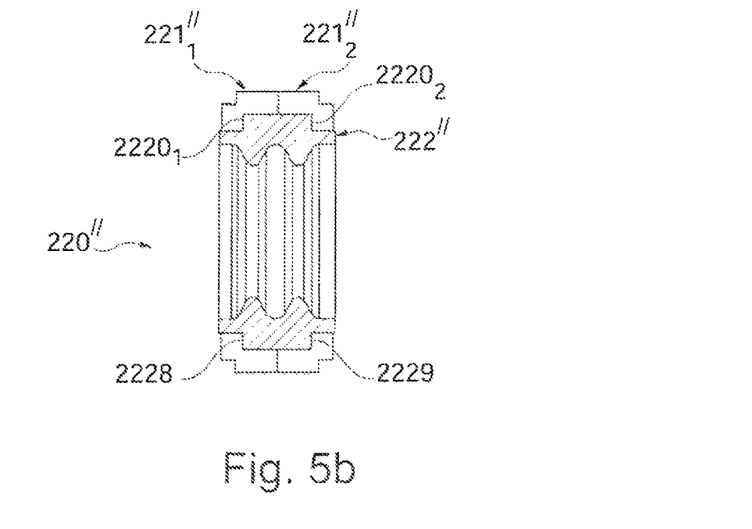

FIGS. 4a, 4b, on the one hand, and FIGS. 5a, 5b, on the other hand, illustrate two alternative embodiments implementing an isolation element, respectively referenced 220' and 220", consisting of two rigid half-sleeves and a flexible seal.

The rigid sleeve of FIGS. 4a and 4b is composed of two identical half-cylindrical sleeves $221'_1$, $221'_2$ having cooperating milled notches $2217_1$, $2217_2$ and projecting lugs $2218_1$, $2218_2$ formed on the inner lateral sides of the half-sleeves, that are assembled together by clipping so the lugs interfit into the notches.

The mating surface profiles for the immobilization of flexible seal 222' include, outer shoulders described above with reference to FIGS. 3a and 3b, the grooves $2227_1$, $2227_2$ carried by the outer annular side of the flexible seal 222' and intended to cooperate with corresponding ribs $2219_1$, $2219_2$ formed on the inner annular sides of the half-sleeves $221'_1$, $221'_2$.

If necessary to increase insulation performance, the sides of flexible seal 221' may also extend beyond the outer lateral sides of the half-sleeves $221'_1$, $221'_2$.

Similarly, the rigid sleeve of FIGS. 5a and 5b is composed of two identical half-cylindrical rigid sleeves $221''_1$, $221''_2$ with internal shoulders $2220_1$, $2220_2$. As for the isolation element 220' of FIGS. 4a and 4b, lugs and notches are used to clip the two half-sleeves $221''_1$, $221''_2$ between them. The flexible seal 222" consists of a part comprising two outer shoulders 2228, 2229. When assembling the two half-sleeves $221''_1$, $221''_2$ and the flexible seal 222", the outer shoulders 2228, 2229 of the seal are positioned against the inner shoulders $2220_1$, $2220_2$ of the half-sleeves, which exert a compression on the seal at the outer shoulders.

To form the connector head 10 of FIGS. 1a and 1b, the elements 100, 210, 220 previously mechanically assembled are overmolded by means of a thermoplastic material such as TECOTHANE. This method can precisely position the various elements in cavity 11 and keep them firmly in position. It also ensures insulation between two electrical contacts 210 and between the electrical contacts and the surrounding environment because the overmolding step creates a chemical bond between rigid sleeves 221 and connector head 10 both made of, e.g., TECOTHANE, in zones 12, called melting zones, as discussed above with reference to FIG. 1b.

Rigid sleeve 221 thus protects flexible seal 222 from pressure and temperature during injection molding or casting.

In practice, the three annular electrical contacts 210 and the four isolation elements 220 are alternately assembled by fitting on a mold pin so as to align them and form a stack 200 as shown in FIGS. 6a and 6b. The isolation elements are surrounded by end caps 301, 302 so that a controlled pressure can be applied to the elements of the stack 200, as necessary and sufficient for enabling a mechanical stop for each element. Under the action of this controlled pressure, the lateral sides 2225, 2226 of the flexible seals 222 are axially compressed, creating a barrier to the leakage and electrical breakdown path. This axial compression also prevents the thermoplastic material of connector head 10 from spilling into the interior of cavity 11 during the overmolding operation. The thus equipped pin with all the stacked elements is placed in the mold with rigid sleeve 110 and the set screw 120. The molding can then be performed.

In summary, the proposed method ensures the coaxiality of the various elements and a precise dimensioning through stack 200 made by interlocking the electrical contact and isolation elements, which also guarantees the compression of flexible seals 222 during their positioning on the pin of the mold. The overmolding provides chemical adhesion creating an electrical insulation to the outer surface cavity 11, at the level of melting zones 12. All the elements constituting the cavity are molded into the final connector head 10, facilitating manufacturing, the latter being reduced to simple operations:

Casting of sleeves, half sleeves, flexible seals and end caps;
    Water jet cutting, EDM for resilient contacts;
    CNC machining for the electrical contact cages, and
    Molding of the assembly into the final mold of the connector head.

Figure 7:
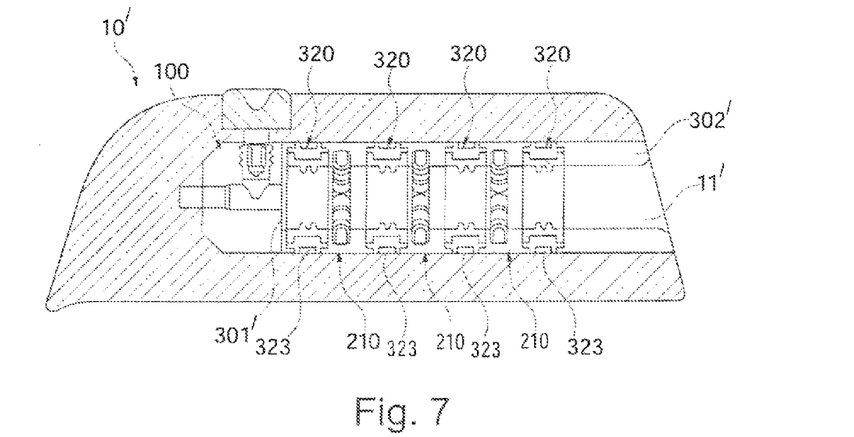
FIG. 7 is a sectional view of a second embodiment of a connector head according to the present invention.
Figure 9A:
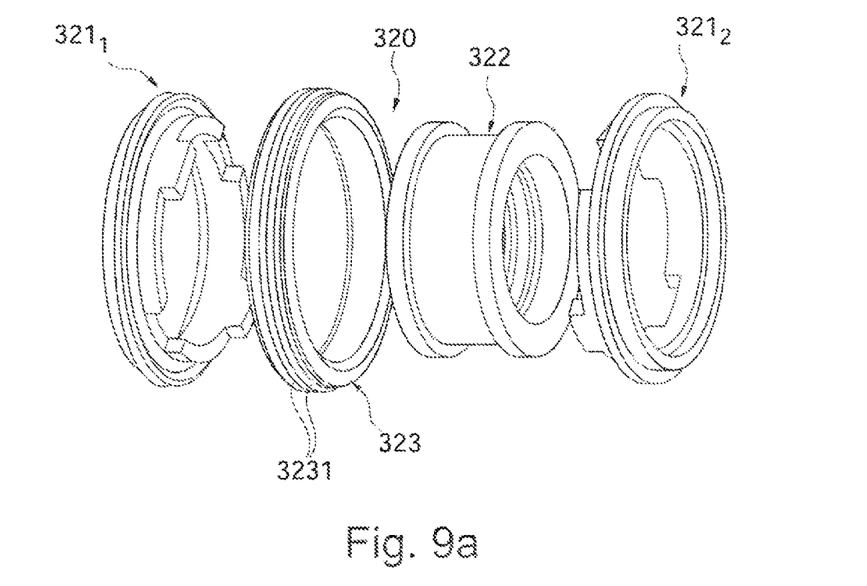
FIG. 9a is an exploded elevated partial cutaway perspective view of an isolation element of the connector head of FIG. 7.
Figure 9B:
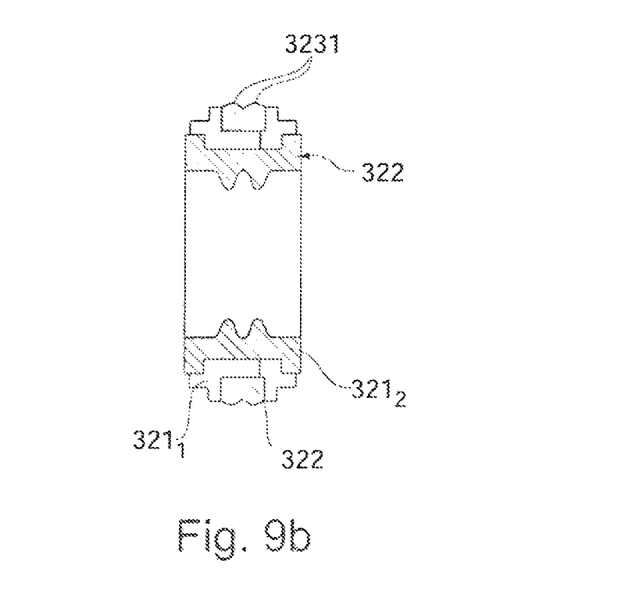

FIG. 7 provides an alternative embodiment of a molded connector head 10' in which the electrical contact elements 210 and the isolation elements 320 are directly inserted in an open cavity 11', preformed in the head 10'. In this embodiment, the isolation elements 320 consist of, as shown in FIGS. 9a and 9b, two half-sleeves $321_1$, $321_2$, similar to those shown in FIGS. 4a, 4b and 5a, 5b. It should be understood that the half-sleeves $321_1$, $321_2$ have on their outer annular side a second flexible seal 323 to allow a seal between electrical contacts 210 and between the cavity 11' and the external environment. The insulation is then obtained by radial compression of sealing rings 3231 of external flexible seal 323.

Figure 8:
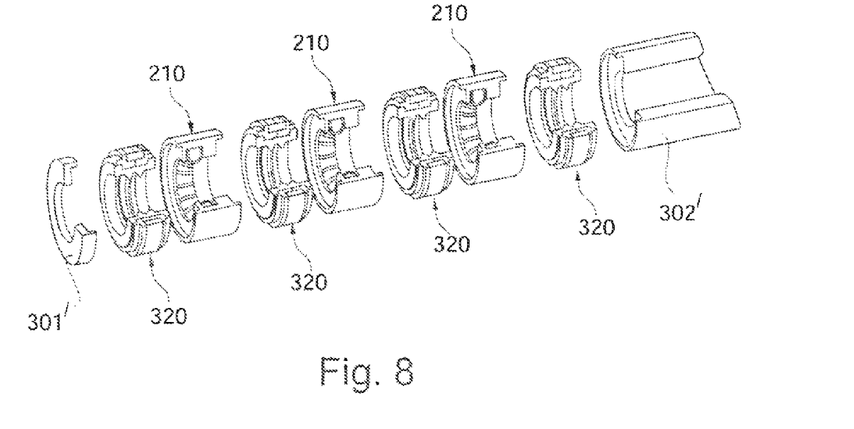
FIG. 8 is an exploded perspective view of a stack of electrical contact and isolation elements of the connector head of FIG. 7.

After insertion into the connector head 10', the annular elements 210, 320 present in the cavity are abutted and held in position between the plugs 301', 302' that can be seen in FIGS. 7 and 8.

One skilled in the art will appreciate that the present invention can be practiced by embodiments other than those described herein, which are provided for purposes of illustration and explanation, and not of limitation.

The invention claimed is:

1. A connector (10) for a generator of an active implantable medical device, comprising a substantially cylindrical cavity (11) for receiving a multipolar lead for an active implantable medical device, said cavity comprising a stack (200) of annular elements (210) including a first number of annular electrical contacts and a second number of annular isolation elements (220, 320), said annular isolation elements being interposed between said annular electrical contacts and isolating said electrical contact elements, wherein:

Each isolation element (220, 320) comprises:
- an annular rigid sleeve (221) having an internal annular side, an internal region, and two lateral sides, and
- an annular flexible seal (222, 322) having two lateral sides and an external annular side disposed against said internal annular side in said internal region of the annual rigid sleeve;

Each flexible seal extends axially from one lateral side of the annular rigid sleeve to the other lateral side of the annular rigid sleeve in said interior region of the annular rigid sleeve, each of said lateral sides (2225, 2226) of the flexible seal projecting with respect to the corresponding lateral sides of the annular rigid sleeve; and The annular rigid sleeve and the flexible seal of an isolation element further comprise respective mating surface profiles defined on a respective inner annular face (2211) of the annular rigid sleeve and on said external annular side (2221) of the flexible seal, thereby immobilising the flexible seal relatively to the annular rigid sleeve in an axial direction.

2. The connector of claim 1, wherein the mating surface profiles further comprise cooperating shoulders (2212, 2213, 2222, 2223) respectively formed on the inner annular side of the annular rigid sleeve and on the outer annular side of the flexible seal.

3. The connector of claim 1, wherein the mating surface profiles comprise cooperating grooves (2227) and ribs (2219) respectively formed on the outer annular side of the flexible seal and on the inner annular side of the annular rigid sleeve.

4. The connector of claim 1 further comprising a second annular flexible seal (323), disposed on the outer annular side of the annular rigid sleeve.

5. The connector of claim 1, wherein the electrical contact elements (210) and the annular rigid sleeves (221) of the isolation elements (220) further comprise interlocking assemblies (2215, 2216, 2112, 2113).

6. The connector of claim 1, wherein the annular rigid sleeve consists of two juxtaposed half-sleeves interconnected.

7. The connector of claim 1, wherein said stack (200) of alternating electrical contact elements (210) and isolation elements (220) comprises an overmolded stack.

8. The connector of claim 1, wherein said stack (200) of alternating electrical contact elements (210) and isolation elements (220) is formed in situ within the cavity (11) by insertion alternatively of electrical contact elements (210) and isolation elements (320).

9. The connector of claim 1, wherein the electrical contact elements (210) further comprise a cage (211) housing a resilient contact (212), the resilient contact comprising a resilient metal part having a U-shape section (2121) wound to form an open cylinder, ensuring a flexible contact function with counterpart conductive rings of a multipolar lead connection plug.

10. The connector of claim 9, wherein the resilient contact (212) comprises a flat sheet of resilient metal cut out so as to form lamellae (2122) and folded in order to obtain the U-shape (2121) and the open cylinder.

11. The connector of claim 9, wherein the cage (211) further comprises two side walls (2114, 2115) forming axial positioning stops for the different adjacent annular isolation elements (220, 320) of the stack.

* * * * *